United States Patent [19]

Lowther

[11] Patent Number: 4,945,306
[45] Date of Patent: Jul. 31, 1990

[54] COIL AND HALL DEVICE CIRCUIT FOR SENSING MAGNETIC FIELDS

[75] Inventor: Frank E. Lowther, Plano, Tex.
[73] Assignee: Atlantic Richfield
[21] Appl. No.: 262,372
[22] Filed: Oct. 25, 1988
[51] Int. Cl.$^5$ .................. G01N 27/83; G01R 33/06
[52] U.S. Cl. ........................... 324/220; 307/309; 324/235; 324/240; 324/251; 324/258; 338/32 H
[58] Field of Search .................... 324/219-221, 324/235, 240, 251, 252, 258, 117 H; 307/309; 338/32 H; 73/DIG. 3

[56] References Cited

U.S. PATENT DOCUMENTS

| 2,814,015 | 11/1957 | Kuhrt | 324/251 X |
| 3,195,043 | 7/1965 | Burig et al. | 307/309 X |
| 4,468,619 | 8/1984 | Reeves | 324/220 |
| 4,789,827 | 12/1988 | Bergander | 324/220 |

FOREIGN PATENT DOCUMENTS

| 849385 | 9/1960 | United Kingdom | 338/32 H |
| 890411 | 2/1962 | United Kingdom | 324/251 |
| 1261346 | 1/1972 | United Kingdom | 324/235 |

Primary Examiner—Gerard R. Strecker

[57] ABSTRACT

Relatively minute changes in magnetic field intensity are sensed by a circuit including a wire coil connected to a Hall effect element to provide the bias current to the element. The Hall effect element is disposed in the magnetic field with the coil and the output signal of the element is proportional to the square of the intensity of the magnetic field. The circuit is included in a device for measuring magnetic anomalies such as stress or corrosion cracks in structures of magnetic material including fluid transmission pipelines.

16 Claims, 2 Drawing Sheets

COIL AND HALL DEVICE CIRCUIT FOR SENSING MAGNETIC FIELDS

BACKGROUND OF THE INVENTION

1. Field of the Invention

The present invention pertains to a sensitive magnetic field detector including a wire coil which provides a bias current to a hall effect device which senses the same incident magnetic field as the coil. The final output signal from the hall effect device is proportional to the square of the magnetic field intensity and provides improved sensitivity of the circuit for applications including detection of magnetic anomalies such as caused by cracks in fluid transmission pipelines.

2. Background

There are many applications of sensors and switching devices in which a minute change in a magnetic field indicates an event or anomaly to be detected. One such application is in detecting stress or corrosion cracks in fluid transmission pipelines and similar structures. It has, for example, been proposed to use a wire coil disposed in a magnetic field which passes through the wall of the pipeline or similar structure in which the crack or anomaly is disposed. The magnetic field is typically passed adjacent to the structure in the area to be sensed and the change in the field caused by the crack or other anomaly generates a current flow which is proportional to the number of turns in the coil, the strength of the magnetic field, and the rate of change in the intensity of the field. However, the sensitivity of a simple coil type detector may not be sufficient in detecting minute cracks in the range of 10 to 100 microinches, particularly considering circuit noise, less than ideal field flux contrast as the detector passes by the crack, flux leakage and the like. Considering these factors the limit of detectability of stress or corrosion cracks in steel pipe may be in the range of 1,000 microinches or greater.

Hall effect devices or elements are also well-known for use in detecting the presence of magnetic fields. Since a Hall device is not flux rate sensitive the detection of an anomaly or crack in a structure by passing a Hall device disposed in a magnetic field which is moving relative to the crack may be confined to rather low relative velocities. However, in certain applications such as detecting cracks in long distance fluid transmission pipelines a minimum practical velocity of the sensing device precludes use of a Hall device alone. For example, in the Trans-Alaska pipeline system the problem of providing an effective crack detector on a pig or a device which is transmitted through the line is apparent. The roughly $10^{10}$ square inches of pipe wall provides $10^{12}$ different positions within which a 0.10 by 0.10 inch crack can hide. The signal noise problem is equally as severe. Benign pipe wall anomalies, vibrations of the detector device, changing surface conditions inside and outside, pipe welds and other anomalies create noise in a crack detection device which may produce multiple false alarms. However, the problems associated with providing means for detecting minute changes in magnetic fields such as would be provided by magnetic crack detector are solved by the unique circuit and device of the present invention.

SUMMARY OF THE INVENTION

The present invention provides an improved device for detecting minute changes in a magnetic field such as might be incurred by a crack or other anomaly in a structure made of magnetic material which is exposed to a magnetic field moving relative to said crack or anomaly. In particular, the present invention provides a unique circuit which is adapted to sense a magnetic field, including minute changes in such a field, whereby a multiplier effect regarding the intensity of the field is sensed by the circuit and used to provide an output signal indicating the presence of the changing field.

The present invention also provides a unique circuit for sensing magnetic fields comprising a coil which is exposed to a changing magnetic field which is connected to a Hall effect device to provide the bias current of the device so that the change in the magnetic field sensed by the coil provides the bias signal to the Hall effect device. The same magnetic field which is sensed by the coil is also imposed on the Hall effect device and a resultant signal output voltage is produced by the circuit which is proportional to the square of the magnetic field intensity. Such a circuit provides improved sensitivity for devices which detect the change or presence of a magnetic field. Such a device, including a noise signal filter circuit in the output circuit from the Hall effect element becomes a particularly suitable device for providing a high signal to noise ratio. The Hall effect elements may be arranged in series to provide a sensitive switch circuit.

Still further in accordance with the present invention there is provided an improved device for detecting the presence of a relatively minute crack in a structure made of magnetic materials such as a fluid transmission pipeline or similar structure.

The present invention still further provides a device for sensing minute changes in a magnetic field caused by passing the magnetic field past a small crack or other anomaly in a structure made of magnetic material wherein the probability of error signals is reduced by an arrangement which in effect causes the signal detector to sweep in a suitable manner so that more than one signal indicating the anomaly is obtained.

The above-mentioned features and advantages of the present invention as well as other superior aspects thereof will be further appreciated by those skilled in the art upon reading the detailed description which follows.

DESCRIPTION OF PREFERRED EMBODIMENTS

Figure 1:
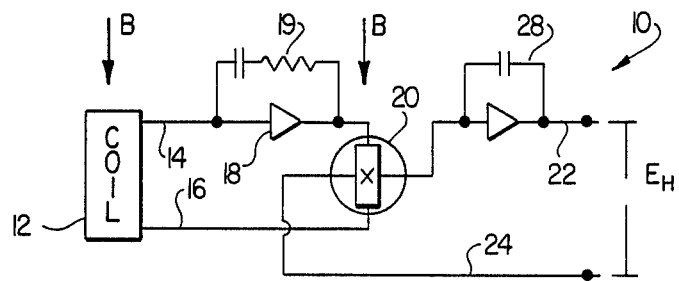
FIG. 1 is a diagram showing the improved coil and Hall device circuit of the present invention.

In the description which follows like parts are marked throughout the specification and drawing with the same reference numerals, respectively. The drawing figures are not necessarily to scale and certain elements are shown in schematic form in the interest of clarity and conciseness.

FIG. 1 illustrates a unique circuit in accordance with the present invention which may be utilized to detect minute changes in a magnetic field. The circuit of FIG. 1 is generally designated by the numeral 10 and is adapted to be exposed to a magnetic field B which is subject to relatively minute changes as well as substantial changes in its intensity. The circuit 10 includes a wire coil 12 which is exposed to the field B and includes output leads 14 and 16. An amplifier 18 may be interposed in the conductor 14 for amplifying the voltage signal generated as a result of a change in the intensity of the magnetic field B as viewed by the coil 12. The conductors 14 and 16 are connected to a Hall effect element 20 to provide the bias current to said element. The Hall effect element 20 is also arranged to be interposed in the magnetic field B and to function in a manner known to those skilled in the art in response to the bias current flowing therethrough to produce an output voltage signal $E_H$ across the conductors 22 and 24. An integrating circuit 28 is interposed in the output circuit from the Hall effect element 20. The amplifier 18 includes a noise filter circuit 19 whereby only signals of a selected bandwidth are imposed on the Hall effect element 20.

The circuit 10 of FIG. 1 produces a voltage which is proportional to the square of the magnetic field B or any change therein. Accordingly, the sensitivity of a circuit such as the circuit 10 is greater than the sensitivity of either a magnetic coil circuit alone or a Hall effect element circuit alone. Moreover, since the Hall element 20 does not significantly change its output signal in response to a change in a magnetic field and the coil responds only to a change in field intensity, the circuit 10 generates very low levels of "noise" signals in many applications such as those described in some detail herein. This sensitivity or output signal may be expressed as follows. The current I produced by a magnetic coil circuit having a coil of N turns exposed to a magnetic field B and a load resistance interposed in the circuit in place of the Hall effect element 20 may be expressed as follows:

$$I = \mu \left( \frac{K_C N \, dB/dt}{R_C + R_L} \right) \quad (1)$$

where
$K_C$ equals the coil constant,
B equals the magnetic field to be measured (in gauss),
N equals the number of turns in the coil,
$R_C$ equals resistance of the coil (ohms),
$R_L$ equals the load resistance (ohms),
$\mu$ equals the gain of the amplifier (current gain) and
t equals time (seconds)

On the other hand the output signal of a Hall effect device may be expressed as follows:

$$E_H = K_H I B \quad (2)$$

where
I equals the bias current (amperes),
B equals the magnetic field to be measured (gauss),
$E_H$ equals the output signal (volts) and
$K_H$ equals the sensitivity constant of the Hall device.

Substituting equation (1) into equation (2) and integrating from 0 to time t provides the equation:

$$E_H = \left( \frac{\mu K_H K_C N}{2(R_C + R_L)} \right) B^2 \quad (3)$$

Figure 2:
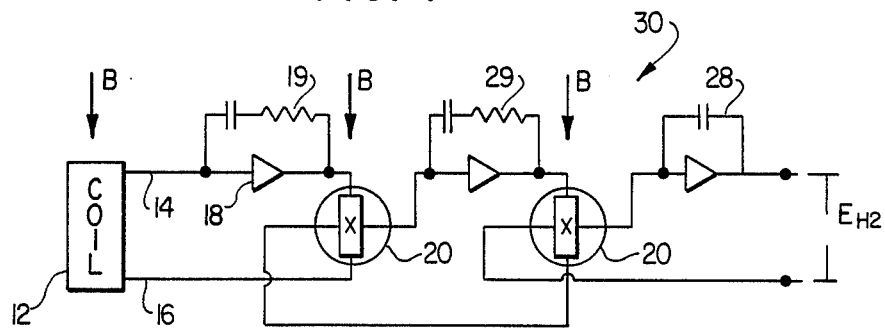
FIG. 2 is a diagram of an alternate embodiment of the circuit of the present invention.

Accordingly, it may be seen from the above that the output signal of the circuit 10 is proportional to the square of the magnetic field intensity B. Moreover, by providing a second Hall element 20 interposed in a circuit 30 similar to the circuit 10, as illustrated in FIG. 2, and wherein the second Hall element 20 is also exposed to the magnetic field B, an output voltage signal $E_{H2}$ may be provided which is proportional to the 3rd power of the intensity of the magnetic field B. The circuit 30 includes a noise signal filter circuit 29 interposed between the two Hall elements and an integrating circuit 28 is connected to the output of the second Hall element. Such a circuit would be particularly useful as a switching device.

Figure 3:
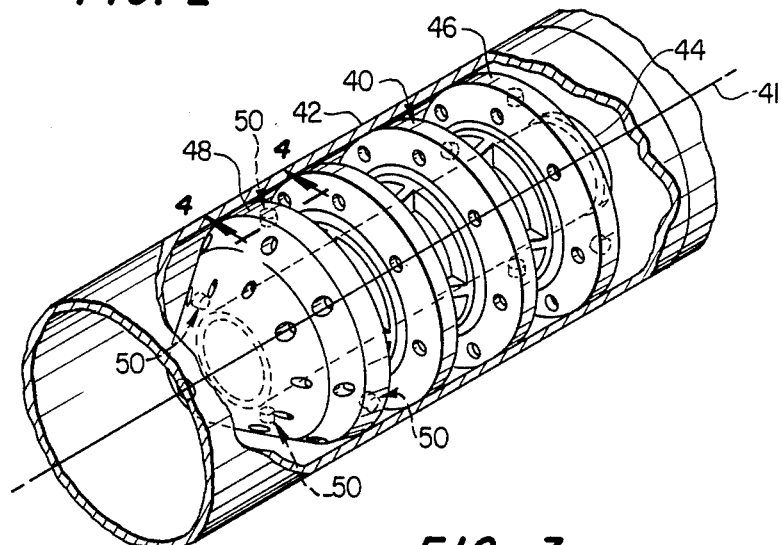
FIG. 3 is a perspective view showing a pipeline survey pig including one, or more crack detection devices of the present invention using the circuit of FIG. 1.
Figure 4:
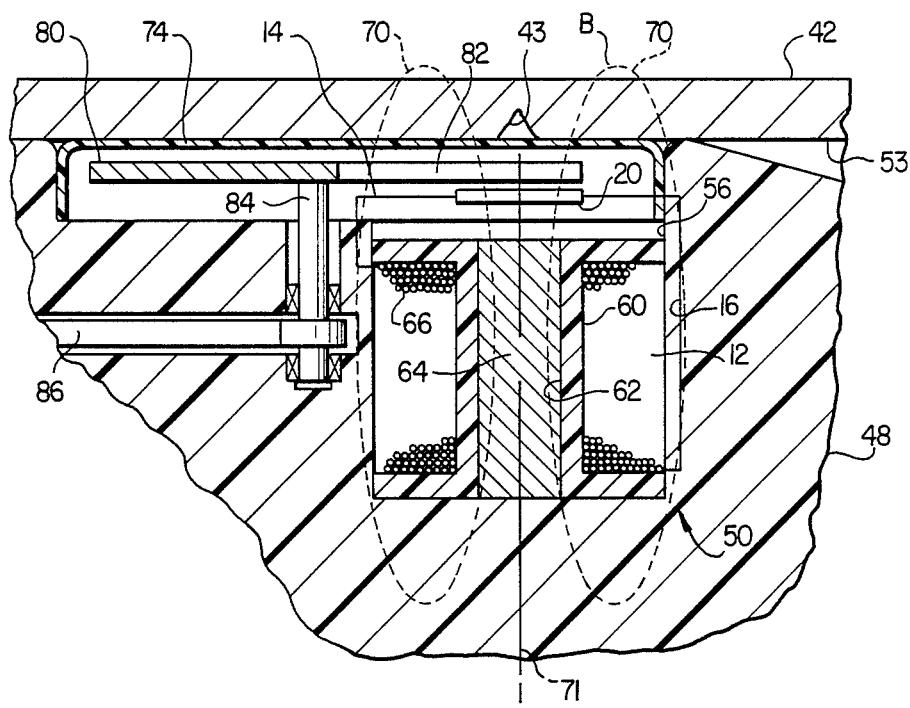
FIG. 4 is a detailed section view of one embodiment of a crack detection device in accordance with the present invention.

Referring now to FIGS. 3 and 4, in FIG. 3 there is illustrated a pipeline survey pig, generally designated by the numeral 40, which is disposed in a cylindrical steel fluid transmission pipeline 42 and is operable to be propelled therethrough by fluid pumped through the pipeline. The survey pig 40 is of generally conventional construction including a body 44 which is supported in the pipeline 42 by a plurality of resilient somewhat cup-shaped support members 46 and 48, by way of example. At least one of the support members 48 is provided, around its periphery, with a plurality of magnetic anomaly or crack detection devices, generally designated by the numeral 50. Each of the devices 50 is disposed in the support member 48 in a manner which is more clearly illustrated in FIG. 4. The number of devices 50 required to scan the circumference of the pipe 42 would, of course, depend on the diameter of the pipe and the support member 48. Other arrangements for scanning the circumference of the pipe wall might result in supporting one or more of the devices 50 in such a way that they are rotated about the longitudinal axis 41 of the pipe 42 to sweep the circumference of the pipe as the survey pig traverses longitudinally therethrough.

Referring now to FIG. 4 the device 50 is illustrated as being disposed in a cavity 56 formed in the support member 48 near the periphery of the support member and adjacent the inner wall surface 53 of the pipe 42. The device 50 includes a wire coil 12 comprising a spool member 60 of non-magnetic material having a hollow central passage 62 in which is disposed a magnet 64. The magnet 64 may be a permanent magnet or an electromagnet as will be discussed further herein. A continuous coil of electrical conductor wire 66 is wound on the spool 60 and is influenced by a generally toroidal shaped magnetic field B which is generally symmetrical with respect to the coil central axis 71, and includes a plurality of magnetic flux lines 70 as indicated schematically in FIG. 4. With the central axis 71 generally normal to the wall of the pipe 42 the flux lines pass through the wall and, upon sensing an anomaly such as a crack 43, the flux intensity changes to produce an output signal across the conductors 14 and 16 indicated in the schematic diagram of FIG. 1. The Hall effect element 20 is shown connected to the output conductors 14 and 16 of the coil 12 and is disposed to also be intersected by the magnetic flux lines 70. The output conductors from the Hall element 20 are not shown in FIG. 4 in the interest of clarity. The cavity 56 is shielded by a cover 74 of nonmagnetic material to prevent contamination of the device 50, and additional structure to be described, by pipeline fluid or material deposited on the wall 53 of the pipe 42.

The embodiment of the invention illustrated in FIG. 4 also includes means which effectively "sweeps" the device 50 with respect to the crack or anomaly 43 desired to be detected to enhance the signal characteristics of the output of the device indicating the presence of the crack 43, for example. One way of providing a sweep of the output signal is to provide a shutter comprising a rotating disk 80 of magnetic material which includes a circular sector shaped opening 82 formed therein. The disk 80 is suitably mounted on a rotatable shaft 84 and driven by suitable means including a drive belt 86 connected to a driving source, not shown, and driven at constant speed as the device 50 is traversed along the pipe 42.

Figure 5:
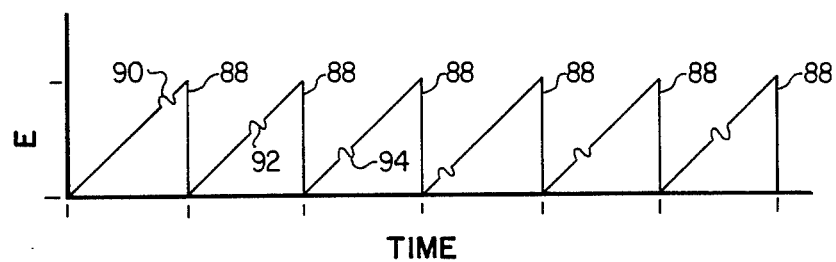
FIG. 5 is a diagram illustrating the output signal characteristic of the device illustrated in FIG. 4.

FIG. 5 illustrates the voltage output signal E of the device 50 as a function of time wherein the substantial interruption of the magnetic field caused by the rotating disk 80 provides a constant repeated sawtooth type output signal as indicated at 88. As the device 50 approaches the crack 43 the signal indicating the disturbance of the magnetic field B caused by the crack 43 is superimposed on the sawtooth signal 88 as indicated at 90, 92, 94 and so on. Certain advantages result from the so-called effective sweeping of the sensing device 50 with respect to the anomaly to be detected. A signal enhancement is provided, particularly for the detecting coil 12 since the effective speed of the coil past the crack is increased and a greater number of signals per crack, or other anomaly to be detected, are provided superimposed on the sweep signal.

The means for sweeping the detector device 50 past the anomaly to be detected as illustrated in FIG. 4 is exemplary. Alternative methods could include physically moving the device 50 with respect to the support member 48 or forming the magnet 64 as an electromagnet and imposing a signal of varying amplitude on the electromagnet to change the intensity of the field B. The individual signals 90, 92, 94 and so on will have a higher amplitude and are narrower in time than the corresponding signal for a non-swept sensing device. However, the sweeping technique also reduces spurious signals and minimizes the requirement for multiple surveys to be conducted to verify a signal.

Figure 6:
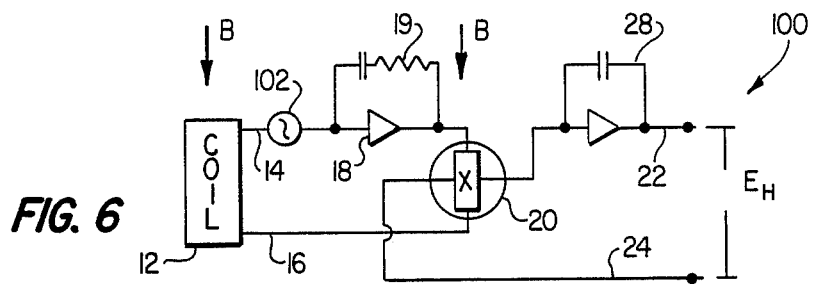
FIG. 6 is a diagram of a second alternate embodiment of a circuit of the present invention.

Referring now to FIG. 6, a second alternate embodiment of a circuit according to the present invention is illustrated and generally designated by the numeral 100. The circuit 100 is similar to the circuit 10 but includes an auxiliary signal source 102 between the coil 12 and the Hall element 20. The source 102 may be a constant or variable DC or AC source for supplying a bias signal to the Hall element when there is no output from the coil 12, for example. Moreover, the source 102 could be varied in signal amplitude, a pulse or AC signal for example, for performing the "sweeping" function described hereinabove. The source 102 may be placed between the amplifier 18 and the Hall element 20, also.

Those skilled in the art will recognize from the foregoing description that a unique sensing circuit device has been provided which utilizes some of the best features of a Hall effect element and a simple electrical coil for sensing magnetic fields. The unique combination of the present invention provides a magnetic field sensing device of improved sensitivity and noise signal rejection and may also be utilized for functions other than that as a magnetic anomaly detector. Although preferred embodiments of the invention have been described herein those skilled in the art will appreciate that various substitutions and modifications may be made to the invention defined in the appended claims without departing from the scope and spirit thereof.

What is claimed is:

1. A circuit for detecting relatively minute changes in the intensity of a magnetic field comprising:
   a coil adapted to be disposed in said magnetic field and including conductor means for conducting a current in response to a change in the magnetic field sensed by said coil;
   a first Hall effect element including means connected to said conductor means of said coil for receiving said current as a bias current imposed on said first Hall effect element; said first Hall effect element being disposed in said magnetic field with said coil;
   output conductor means connected to said first Hall effect element for producing a voltage signal which is proportional to the intensity of said magnetic field; and
   at least a second Hall effect element disposed in said magnetic field and having means connected to said output conductor means of said first Hall effect element for receiving as a bias current imposed on said second Hall effect element a current produced by said voltage signal output by said first Hall effect element, said second Hall effect element including output conductor means for producing a voltage signal proportional to an exponential power of said magnetic field.

2. The circuit set forth in claim 1 including:
   a noise bandwidth filter for filtering a selected frequency band of signals output from said coil in response to sensing changes in said magnetic field.

3. The circuit set forth in claim 1 including:
   amplifier means interposed in said conductor means of said coil for amplifying the output signal of said coil responsive to a change in said magnetic field.

4. A device for sensing a relatively minute change in a magnetic field passing through a member formed of a magnetic material, which change is caused by a magnetic anomaly associated with said magnetic material, said device comprising:
   a wire coil arranged to be disposed in said magnetic field and in proximity to said member;
   means for producing a magnetic field passing through said member and said coil;
   a Hall effect element disposed in said magnetic field, said Hall effect element including conductor means connected to said coil for conducting a current to said Hall effect element as a bias current and which is produced by a voltage signal generated in said coil as a result of a change in the intensity of said magnetic field;
   signal output conductor means connected to said Hall effect element for producing a voltage across said signal output conductor means; and
   an integrating circuit connected to said Hall effect element for integrating the signal output from said Hall effect element to provide a voltage across said output conductor means proportional to said change in the intensity of said magnetic field.

5. The device set forth in claim 4 including:
   a bandwidth filter for filtering signals of a selected frequency band out of the signal provided at said signal output conductor means.

6. The device set forth in claim 4 wherein:
said means for providing said magnetic field comprises magnet means disposed within said coil.

7. The device set forth in claim 6 wherein:
said magnet means comprises a permanent magnet disposed in a cavity formed by said coil for producing a toroidal magnetic field with respect to the central axis of said coil.

8. The device set forth in claim 6 wherein:
said Hall effect element is disposed in said magnetic field adjacent to said coil.

9. The device set forth in claim 8 including:
means interposed in said magnetic field for interrupting said magnetic field at a predetermined cyclical rate.

10. The device set forth in claim 9 wherein:
said means for interrupting said magnetic field comprises a rotating disk including means forming an opening in said disk whereby a change in the intensity of said magnetic field is provided at a predetermined rate and magnitude to provide a repetitive signal of predetermined rate and magnitude superimposed on a second signal indicating the presence of said magnetic anomaly.

11. A device for use on a survey pig for detecting the presence of a crack in the wall of a fluid transmission pipeline, said pig including support means for supporting said device adjacent to said wall and means for generating a magnetic field imposed on said wall, said device comprising:
a wire coil disposed on said support means in said magnetic field and in proximity to said wall;
a Hall effect element disposed in said magnetic field, said Hall effect element including conductor means connected to said coil for conducting a current to said Hall effect element as a bias current and which is produced by a voltage signal generated in said coil as a result of a change in the intensity of said magnetic field; and
signal output conductor means connected to said Hall effect element for producing a voltage signal across said signal output conductor means proportional to said change in the intensity of said magnetic field.

12. The device set forth in claim 11 including:
a bandwidth filter for filtering signals of a selected frequency band out of the signal provided at said signal output conductor means.

13. The device as set forth in claim 11 wherein:
said means for generating said magnetic field comprises a permanent magnet disposed in a cavity formed by said coil for producing a toroidal magnetic field with respect to the central axis of said coil.

14. The device set forth in claim 11 including:
means interposed in said magnetic field for interrupting said magnetic field at a predetermined cyclical rate.

15. The device set forth in claim 14 wherein:
said means for interrupting said magnetic field comprises a rotating disk including means forming an opening in said disk whereby a change in the intensity of said magnetic field is provided at a predetermined rate and magnitude to provide a repetitive signal of predetermined rate and magnitude superimposed on a second signal indicating the presence of a crack in said wall.

16. A circuit for detecting relatively minute changes in the intensity of a magnetic field comprising:
a coil adapted to be disposed in said magnetic field and including conductor means for conducting a current in response to a change in the magnetic field sensed by said coil;
a Hall effect element including means connected to said conductor means of said coil for receiving said current as a bias current imposed on said Hall effect element, said Hall effect element being disposed in said magnetic field with said coil;
output conductor means connected to said Hall effect element for producing a voltage signal which is proportional to the intensity of said magnetic field; and
means interposed in said magnetic field for changing the effective intensity of said magnetic field sensed by said coil and said Hall effect element and of a magnitude and at a repetitive rate such that other changes in the intensity of said magnetic field produce a signal output of said Hall effect element which is superimposed on a signal output resulting from said means for changing said effective intensity.

* * * * *